(12) United States Patent
Bender et al.

(10) Patent No.: US 11,931,690 B2
(45) Date of Patent: *Mar. 19, 2024

(54) AIR IONIZATION SYSTEM AND DEVICE

(71) Applicant: IONaer International Arizona, LLC, Scottsdale, AZ (US)

(72) Inventors: Timothy M. Bender, Scottsdale, AZ (US); Brian K. Roper, Phoenix, AZ (US); Todd K. Roper, Glendale, AZ (US); Perry Pauley, Glendale, AZ (US)

(73) Assignee: IONaer International Arizona, LLC, Scottsdale, AZ (US)

( * ) Notice: Subject to any disclaimer, the term of this patent is extended or adjusted under 35 U.S.C. 154(b) by 354 days.

This patent is subject to a terminal disclaimer.

(21) Appl. No.: 17/239,455

(22) Filed: Apr. 23, 2021

(65) Prior Publication Data
US 2021/0236988 A1 Aug. 5, 2021

Related U.S. Application Data

(63) Continuation of application No. 16/446,555, filed on Jun. 19, 2019, now Pat. No. 11,007,478, which is a
(Continued)

(51) Int. Cl.
*B01D 53/32* (2006.01)
*A61L 9/00* (2006.01)
(Continued)

(52) U.S. Cl.
CPC .............. *B01D 53/32* (2013.01); *A61L 9/00* (2013.01); *A61L 9/22* (2013.01); *B01D 46/0027* (2013.01);
(Continued)

(58) Field of Classification Search
CPC .............. B01D 53/32; F24F 8/192; A61L 9/22
See application file for complete search history.

(56) References Cited

U.S. PATENT DOCUMENTS 6,791,815 B1 9/2004 Graham
8,048,370 B1 11/2011 Barnes
(Continued)

FOREIGN PATENT DOCUMENTS

CN 104907173 B 9/2015
CN 107062483 A 8/2017
(Continued)

OTHER PUBLICATIONS

USPTO; Non-Final Office Action dated Jun. 30, 2017 in U.S. Appl. No. 15/156,735.
(Continued)

*Primary Examiner* — Kevin Joyner
(74) *Attorney, Agent, or Firm* — SNELL & WILMER L.L.P.

(57) ABSTRACT

An ionization device may be configured to be portable, and to rest on a surface such as a floor or desk top. The ionization device includes an air-intake port, an ion generator, an ozone catalyst for removing at least some ozone from air, and an air discharge. Air enters the device through the air-intake port, and at least some of the air is ionized to remove particulates. The air is then moved past or through the ozone catalyst to remove at least some of the ozone from the air. A controller may be used to monitor particulates, temperature, humidity, and/or other relevant factors and/or to adjust the ionization level.

23 Claims, 17 Drawing Sheets

Related U.S. Application Data continuation-in-part of application No. 15/914,682, filed on Mar. 7, 2018, now Pat. No. 10,363,332, and a continuation-in-part of application No. 15/913,733, filed on Mar. 6, 2018, now Pat. No. 10,363,522, and a continuation-in-part of application No. 15/913,677, filed on Mar. 6, 2018, now Pat. No. 10,357,586, and a continuation-in-part of application No. 15/622,025, filed on Jun. 13, 2017, now Pat. No. 10,406,476, and a continuation-in-part of application No. 15/622,027, filed on Jun. 13, 2017, now Pat. No. 10,350,541.

(51) Int. Cl.

| | | |
|---|---|---|
| *A61L 9/22* | (2006.01) | |
| *B01D 46/00* | (2022.01) | |
| *B01D 53/30* | (2006.01) | |
| *B01D 53/86* | (2006.01) | |
| *F24F 8/192* | (2021.01) | |
| *H01T 23/00* | (2006.01) | |
| *B01D 53/88* | (2006.01) | |
| *F24F 8/30* | (2021.01) | |
| *F24F 8/98* | (2021.01) | |

(52) U.S. Cl.
CPC ..... *B01D 46/0028* (2013.01); *B01D 46/0038* (2013.01); *B01D 53/30* (2013.01); *B01D 53/323* (2013.01); *B01D 53/8675* (2013.01); *F24F 8/192* (2021.01); *H01T 23/00* (2013.01); *A61L 2209/11* (2013.01); *A61L 2209/13* (2013.01); *A61L 2209/14* (2013.01); *B01D 53/88* (2013.01); *B01D 2255/2073* (2013.01); *B01D 2255/20761* (2013.01); *B01D 2257/106* (2013.01); *B01D 2257/90* (2013.01); *B01D 2258/06* (2013.01); *B01D 2259/4508* (2013.01); *B01D 2259/80* (2013.01); *B01D 2259/818* (2013.01); *F24F 8/30* (2021.01); *F24F 8/98* (2021.01)

(56) References Cited

U.S. PATENT DOCUMENTS

| | | |
|---|---|---|
| 8,747,754 B2 | 6/2014 | Abate |
| 9,907,874 B2 | 3/2018 | Bender et al. |
| 9,908,081 B2 | 3/2018 | Bender et al. |
| 9,908,082 B2 | 3/2018 | Bender et al. |
| 10,350,541 B2 | 7/2019 | Bender et al. |
| 10,357,586 B2 | 7/2019 | Bender et al. |
| 10,363,332 B2 | 7/2019 | Bender et al. |
| 10,363,522 B2 | 7/2019 | Bender et al. |
| 10,406,476 B2 | 9/2019 | Bender et al. |
| 2001/0031234 A1 | 10/2001 | Christodoulatos et al. |
| 2003/0106788 A1 | 6/2003 | Babko-Malyi |
| 2004/0007000 A1 | 1/2004 | Takeda et al. |
| 2004/0247497 A1 | 12/2004 | Yuen |
| 2007/0253860 A1 | 11/2007 | Schroder |
| 2008/0035472 A1 | 2/2008 | Lepage |
| 2008/0063577 A1 | 3/2008 | Crowe |
| 2008/0317802 A1 | 12/2008 | Lee et al. |
| 2009/0202397 A1 | 8/2009 | Parker et al. |
| 2010/0089240 A1 | 4/2010 | Krichatofovitch |
| 2014/0198426 A1 | 7/2014 | Abate |
| 2015/0017059 A1 | 1/2015 | Arlemark |
| 2015/0076082 A1 | 3/2015 | Loucaides |
| 2016/0067645 A1 | 3/2016 | Mutha et al. |
| 2016/0263263 A1 | 9/2016 | Robert |
| 2017/0189846 A1 | 7/2017 | Cho et al. |
| 2017/0217284 A1 | 8/2017 | Ji et al. |
| 2017/0321877 A1 | 11/2017 | Bender et al. |
| 2017/0333587 A1 | 11/2017 | Bender et al. |
| 2017/0333837 A1 | 11/2017 | Bender et al. |
| 2017/0333838 A1 | 11/2017 | Bender et al. |
| 2017/0348636 A1 | 12/2017 | Bender et al. |
| 2018/0036677 A1 | 2/2018 | Bender et al. |
| 2018/0193508 A1 | 7/2018 | Bender et al. |
| 2018/0193509 A1 | 7/2018 | Bender et al. |
| 2018/0193794 A1 | 7/2018 | Bender et al. |
| 2019/0374669 A1 | 12/2019 | Bender et al. |
| 2020/0009502 A1 | 1/2020 | Bender et al. |
| 2020/0009503 A1 | 1/2020 | Bender et al. |

FOREIGN PATENT DOCUMENTS

| | | |
|---|---|---|
| CN | 206583003 U | 10/2017 |
| CN | 113685986 A | 11/2021 |
| JP | S59193158 A | 11/1984 |
| KR | 101461849 B1 | 11/2014 |
| KR | 20160014336 A | 2/2016 |
| KR | 20180007206 A | 1/2018 |
| KR | 102238936 B1 | 4/2021 |
| WO | 2016183237 A1 | 11/2016 |
| WO | 2019147501 A1 | 8/2019 |

OTHER PUBLICATIONS

USPTO; Notice of Allowance dated Dec. 20, 2017 in U.S. Appl. No. 15/156,735.
USPTO; Non-Final Office Action dated Jun. 30, 2017 in U.S. Appl. No. 15/156,755.
USPTO; Notice of Allowance dated Dec. 7, 2017 in U.S. Appl. No. 15/156,755.
USPTO; Non-Final Office Action dated Jul. 24, 2017 in U.S. Appl. No. 15/156,771.
USPTO; Notice of Allowance dated Dec. 7, 2017 in U.S. Appl. No. 15/156,771.
USPTO; Non-Final Office Action dated Nov. 28, 2018 in U.S. Appl. No. 15/622,027.
USPTO; Notice of Allowance dated Apr. 5, 2019 in U.S. Appl. No. 15/622,027.
USPTO; Non-Final Office Action dated Nov. 28, 2018 in U.S. Appl. No. 15/622,025.
USPTO; Notice of Allowance dated Jul. 17, 2019 in U.S. Appl. No. 15/622,025.
USPTO; Non-Final Office Action dated Nov. 30, 2018 in U.S. Appl. No. 15/914,682.
USPTO; Notice of Allowance dated Jun. 12, 2019 in U.S. Appl. No. 15/914,682.
USPTO; Non-Final Office Action dated Dec. 3, 2018 in U.S. Appl. No. 15/913,677.
USPTO; Notice of Allowance dated Apr. 5, 2019 in U.S. Appl. No. 15/913,677.
USPTO; Non-Final Office Action dated Dec. 3, 2018 in U.S. Appl. No. 15/913,733.
USPTO; Notice of Allowance dated Jun. 12, 2019 in U.S. Appl. No. 15/913,733.
USPTO; Non-Final Office Action dated Nov. 6, 2020 in U.S. Appl. No. 16/510,785.
USPTO; Non-Final Office Action dated Aug. 6, 2020 in U.S. Appl. No. 16/510,803.
USPTO; Non-Final Office Action dated Oct. 28, 2020 in U.S. Appl. No. 16/446,555.
USPTO; Notice of Allowance dated Mar. 22, 2021 in U.S. Appl. No. 16/446,555.

AIR IONIZATION SYSTEM AND DEVICE

CROSS-REFERENCE TO RELATED APPLICATIONS

This application claims priority to and is a continuation of Ser. No. 16/446,555, filed on Jun. 19, 2019, entitled "AIR IONIZATION SYSTEM AND DEVICE," which claims priority to and is a continuation-in-part of U.S. patent application Ser. No. 15/913,677, filed on Mar. 6, 2018, entitled "AIR IONIZATION SYSTEMS AND METHODS," which claims priority to and is a continuation-in-part of U.S. patent application Ser. No. 15/913,733, filed on Mar. 6, 2018, entitled "AIR IONIZATION SYSTEMS AND METHODS," which claims priority to and is a continuation-in-part of U.S. patent application Ser. No. 15/914,682, filed on Mar. 7, 2018 entitled "AIR IONIZATION SYSTEM," which claims priority to and is a continuation-in-part of U.S. patent application Ser. No. 15/622,025, filed on Jun. 13, 2017, entitled "AIR IONIZATION SYSTEMS AND COMPONENTS," which claims priority to and is a continuation-in-part of U.S. patent application Ser. No. 15/622,027, filed on Jun. 13, 2017, entitled "AIR IONIZATION SYSTEMS AND COMPONENTS." Each of the foregoing applications are incorporated herein by reference in their entirety. This application also incorporates by reference in their entireties, U.S. Pat. No. 9,907,874, issued Mar. 6, 2018, entitled "AIR IONIZATION SYSTEMS AND METHODS," U.S. Pat. No. 9,908,081, issued Mar. 6, 2018, entitled "AIR IONIZATION METHODS," and U.S. Pat. No. 9,908,082, issued Mar. 6, 2018, entitled "AIR IONIZATION SYSTEM."

BACKGROUND

Prior approaches to air filtration and/or ionization suffer from one or more drawbacks. For example, certain air ionization systems, in order to avoid releasing an unacceptable level of ozone, generate ionization levels that are insufficient to fully clean and/or sanitize a particular air stream. Moreover, other air ionization systems have suffered from a lack of configurability and/or intelligent control. Some air ionization systems have been complex, expensive, and/or lacking in modular configuration and/or serviceability.

SUMMARY OF THE INVENTION

An air ionization device (sometimes referred to herein as "device") is preferably a self-standing, portable unit that can rest on a surface, such as a desk top or floor. The preferred device has a housing, an inner cavity, an air-intake port, an air discharge, and an air ionization unit (or "unit") in the inner cavity, wherein the unit includes an ion generator and an ozone catalyst for removing ozone. The unit may be a one-piece assembly that mounts in the inner cavity of the device, and can be preferably removed and replaced as one piece.

Air enters the inner cavity of the device through the air-intake port and is moved past the ion generator, which ionizes the air to remove particulates. The air then moves through (or otherwise comes into contact with) the ozone catalyst to remove some or all of the ozone. The air is then moved through a discharge and back into the space (such as a room) in which the device is positioned. Inside the inner cavity, the air is preferably moved by one or more fans. In one embodiment there is at least one fan, and most preferably two fans, preferably positioned beneath the ion generator. The fan(s) blow the air upwards towards and into contact with the ion generator. The air pressure then pushes the air outward into contact with the ozone catalyst, and then out of the discharge. The air may be filtered prior to and/or after being ionized such as by a filter at the intake port and/or at the discharge and/or between the fan and the ion generator.

The invention may also include a controller (or "control system") that does one or more of the following: (1) measures the amount of particulate in the air, (2) measures the amount of negative and/or positive ions in the air, (3) measures the amount of ozone in the air, (4) measures the amount of carbon monoxide in the air, (5) measures the air temperature and humidity, and (6) adjusts the amount of ions being released into the air based on one or more of the preceding measured parameters. The controller may be part of, or remote to, the air ionization device.

The contents of this summary section are provided only as an introduction to the disclosure, and are not intended to limit the scope of the claims.

DETAILED DESCRIPTION

The following description is of exemplary embodiments only and is not intended to limit the scope or definition of the claims.

Turning now to FIGS. 1 through 7, an air ionization device (or "device") 1000 is shown. Air ionization device 1000 comprises an outer housing 1002, an ion generator 100, and an ozone removal catalyst 408, which is preferably included in an ozone removal assembly 400. The outer housing 1002 has a first portion 1004, which as shown includes the back 1010 and side walls 1014 of outer housing 1002 and a second portion 1006, which in this embodiment forms the top of outer housing 1002. First portion 1004 and second portion 1006 each is preferably comprised of any type or types of suitable materials, such as aluminum, steel, and/or plastic such as PVC.

An annular mesh facing 1016, through which air can pass, acts as the primary air discharge from device 1000. Facing 1016 is preferably comprised of stainless steel, but can preferably be any electrically-neutral material that does not attract ions, or may be any other suitable material.

Second portion 1006 includes a top section 1006A and a slanted section 1008. Top section 1006A may be of any suitable size or configuration and as shown is slightly curved. Slanted (or angled) section 1008 is preferably formed at a 30°-60°, or about 45°, angle as measured from the horizontal axis. Slanted section 1008 may be of any suitable size, configuration and angle. Slanted section 1008 includes a first opening 1008A, through which the controller and display 1060 may be seen, and possibly controlled by using buttons or a touch screen, when device 1000 is assembled. Slanted section 1008 also includes a recess 1008B, into which a plate or sticker including a company name or logo may be placed, as shown, for example, in FIG. 6.

Back 1010 is preferably part of portion 1004 and has a bottom panel 1010A with an opening 1010B, and an upper panel 1012 with an opening 1011. Back 1010 preferably has one or more (and preferably three) louvered openings 1011A, although any suitable opening(s) may be utilized. Air enters the one or more openings 1011A and comes into contact with an air sensor on sensor circuit board 1050. Side walls 1014 as shown are integrally formed with back 1010, although they could be separate components.

Figure 1:
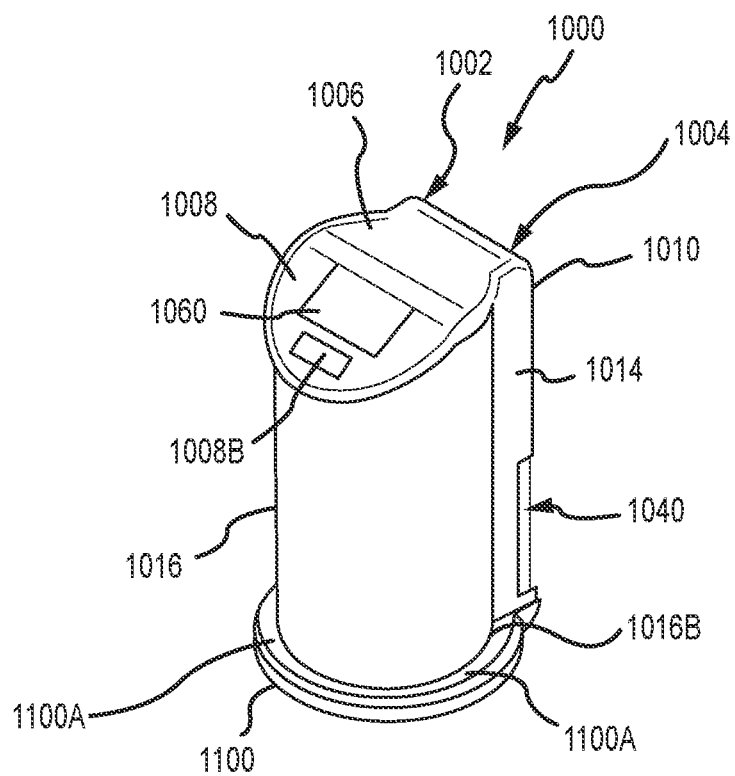
FIG. 1 is an assembled, front perspective side view of an air ionization device in accordance with aspects of the invention.
Figure 2:
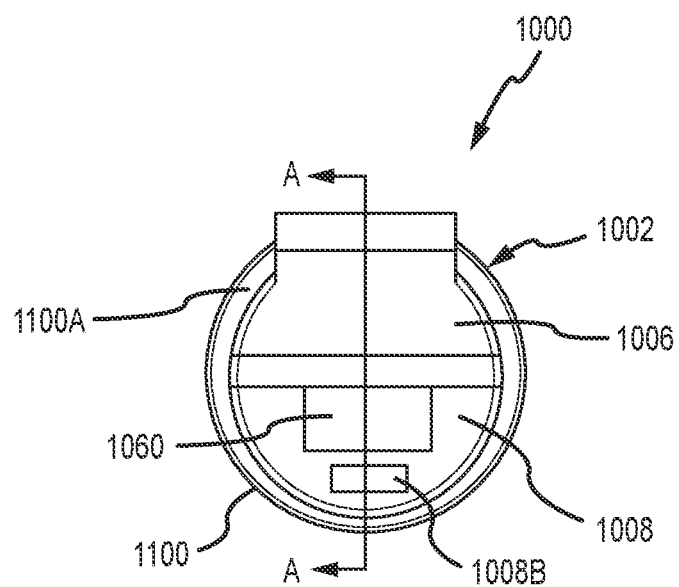
FIG. 2 is a top view of the air ionization device of FIG. 1.
Figure 3:
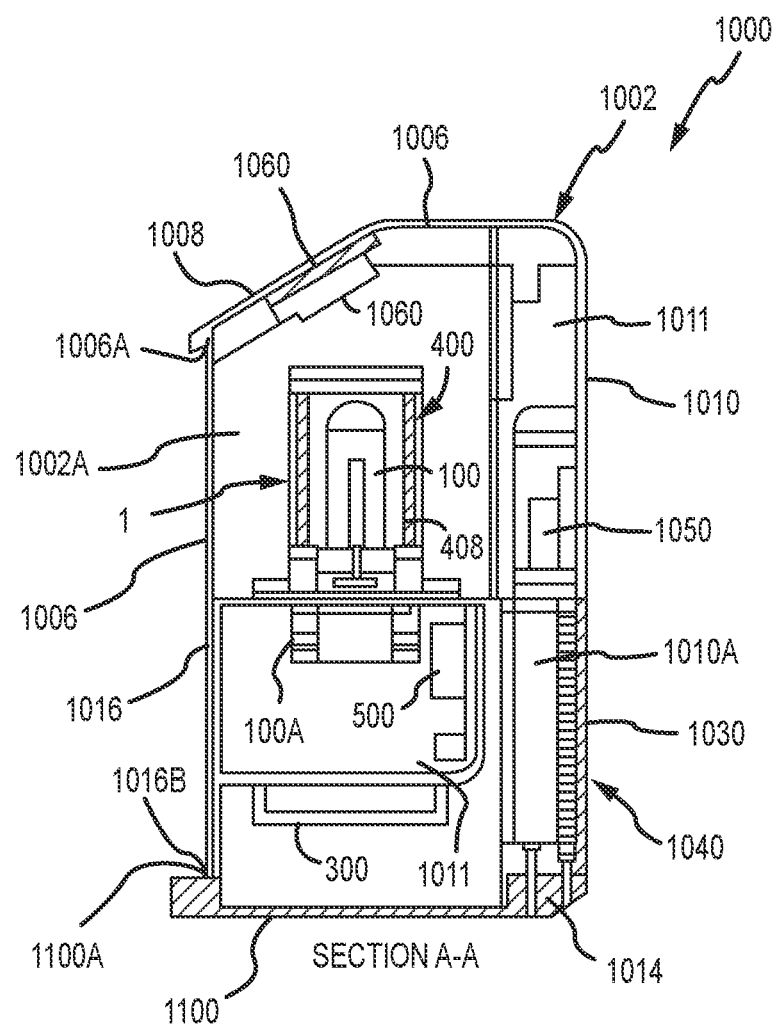
FIG. 3 is a cross-sectional, side view of the air ionization device of FIG. 1 taken along lines A-A.
Figure 4:
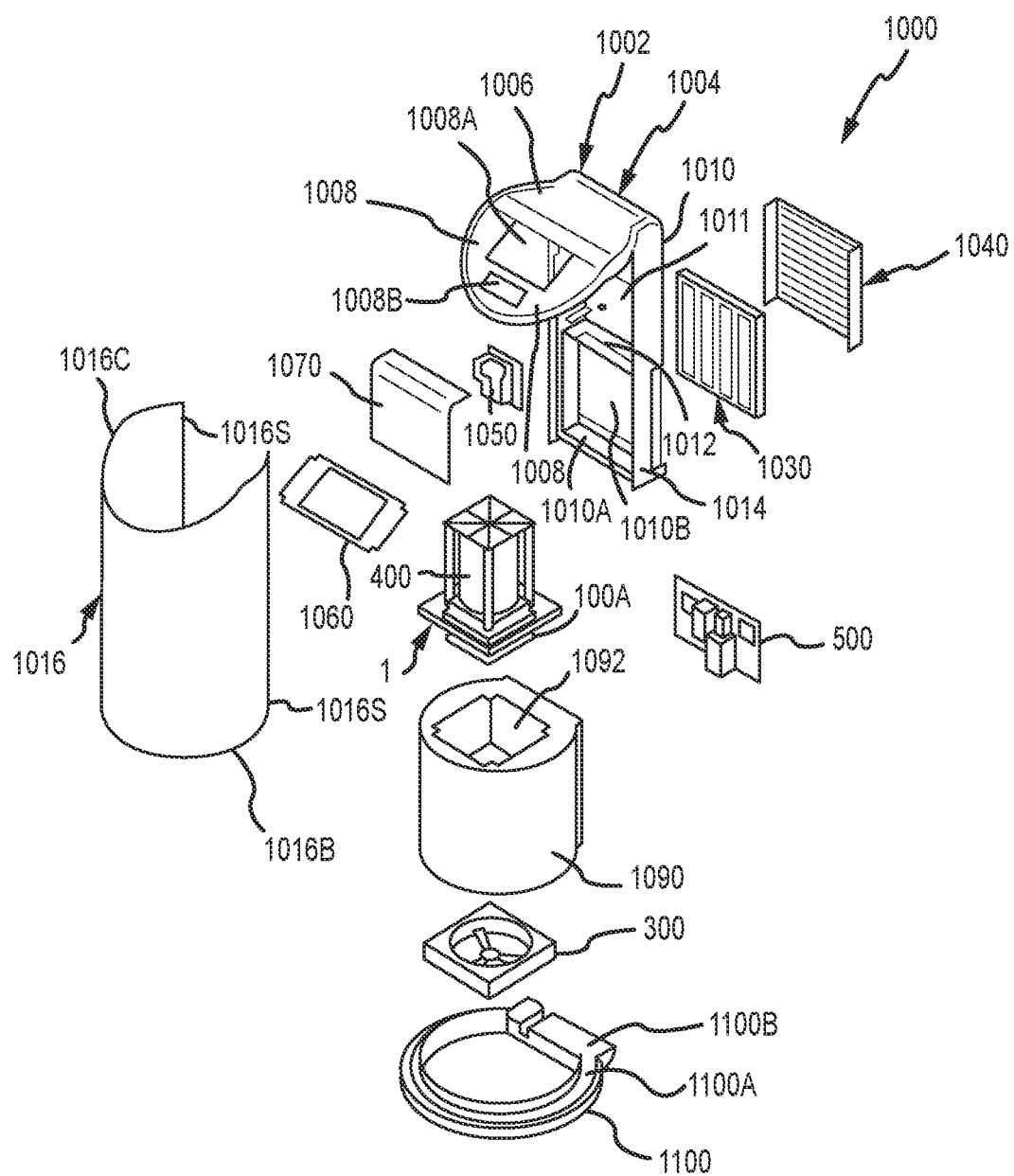
FIG. 4 is an exploded view of an air ionization unit in accordance with embodiments of the invention.
Figure 5:
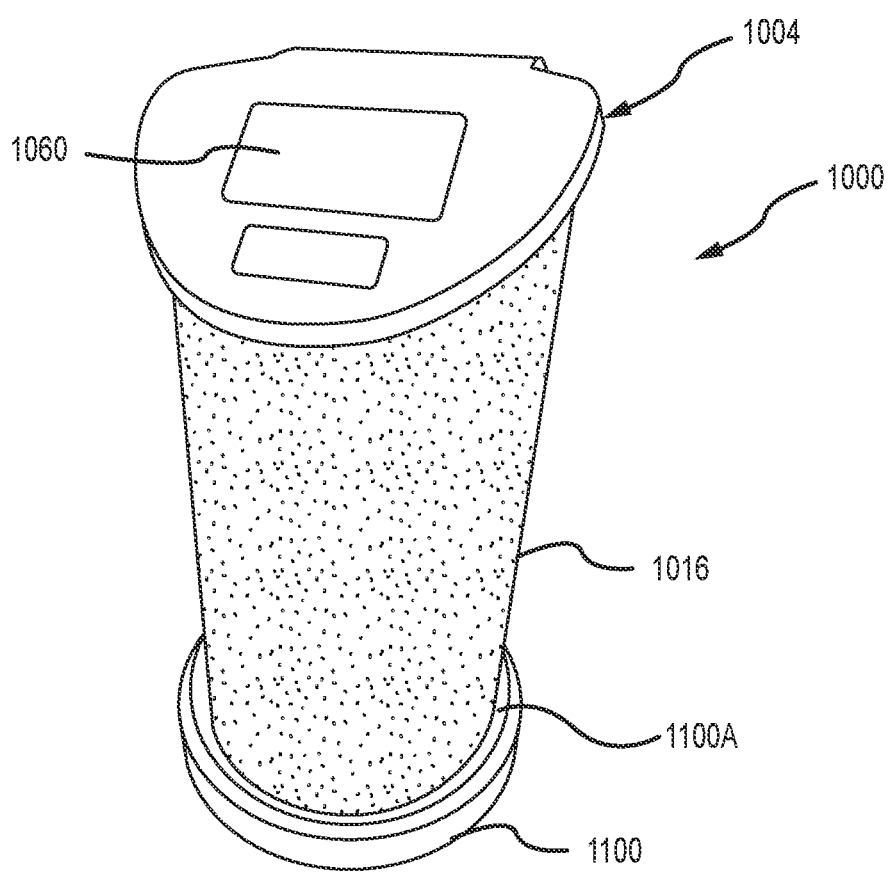
FIG. 5 is a front, perspective view of the device of FIG. 1.
Figure 6:
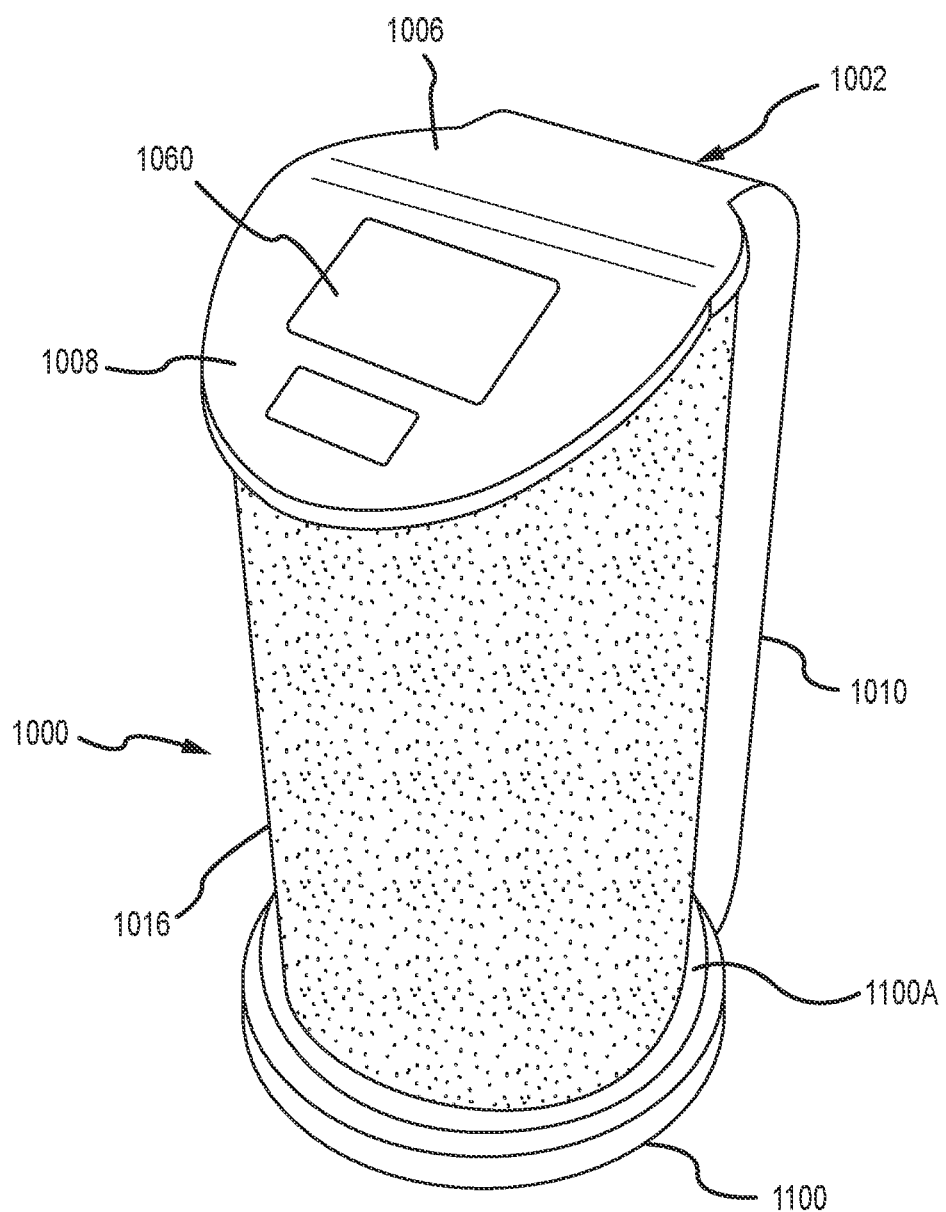
FIG. 6 is a front, perspective view of the device of FIG. 1 with an alternate facing.
Figure 7:
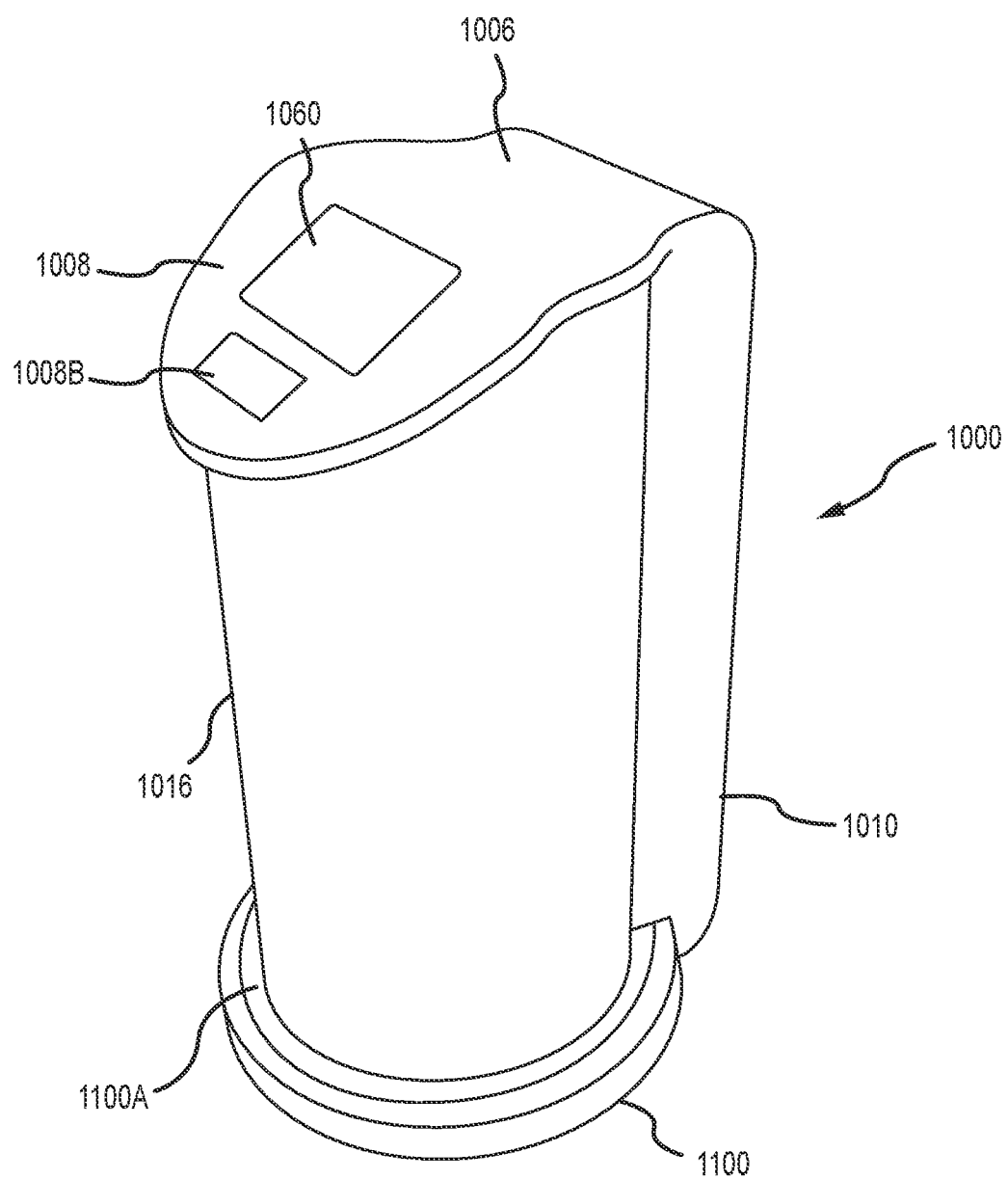
FIG. 7 is an alternate, perspective view of the device of FIG. 1 showing controls on the top.

An inner cavity 1002A is defined inside of outer housing 1002. Ionization unit 100, fan 300, controller circuit board assembly 500, controller and display 1060, portion 1010, and plenum 1090, are positioned in cavity 1002A when device 1000 is assembled, as can be seen in FIG. 3. A plenum 1090 has a cavity 1092 that retains ionization unit 1 (which is described in more detail below). A fan 300 is mounted at the bottom of plenum 1090 and a space is maintained between fan 300 and ionization unit 1.

An air filter 1030 is configured to be retained in opening 1010B by any suitable attachment apparatus. Air filter 1030 is configured to clean air entering the inner cavity 1002A of housing 1002. As shown a filter access grid 1040 fits over air filter 1030 and retains it in place in opening 1010B. The air filter 1030 can be accessed and replaced by removing filter access grid 1040. In this embodiment, most of the air entering inner cavity 1002A enters through opening 1010B. opening 1010B is thus sometimes referred to as an air-intake port.

A base 1100 as shown is a separate component and is configured with a groove 1100A to locate and receive the bottom edge 1016B of facing 1016. Back 1010 and side walls 1014 are screwed or otherwise secured to flat section 1100B of base 1100.

The underside 1006A of sections 1006 and 1008 has a lip 1006B configured to receive the top edge 1016C of facing 1016, as can be seen in FIG. 3. Each side wall 1014 has an edge 1014A with a channel 1014B configured to receive a side edge 1060S of facing 1016. In this manner, the facing 1016 can be independently removed and attached to base 1100, sections 1006, 1008, and side walls 1014, so that inner cavity 1002A can be accessed (for example, to replace ionization unit 1, fan 300, and/or plenum 1090) by removing facing 1016. Also, facing 1016 may be changed so that it has a color, material, design, logo, or other feature desired by a particular customer.

Sensor circuit board 1050 is configured, along with controller circuit board 500, and the controller of controller and display 1060, to control the operation of device 1000. The sensor circuit board 1050 includes one or more sensors that can determine one or more of the air's humidity, temperature, ozone level, particulate amount, particulate density, type of particulate, and/or other parameters. This information can be used to automatically or manually adjust the operation of device 1000.

Controller 1060 preferably includes a WIFI and/or Bluetooth, and/or other communications (such as other RF communications) device. Controller 1060 could also communicate through wired connections, including ethernet over wire communications. Controller 1060 can interface with a router, cell phone, or any suitable device or network.

As best seen in FIG. 3, the partition 1070 fits into panel 1012 with sensor circuit board 1050 inside. This protects sensor circuit board 1050 from directly contracting air circulated in inner cavity 1002A because sensor circuit board 1050 preferably includes one or more sensors to measure parameters of the air in the space in which device 1000 is positioned. A controller circuit board assembly (or assembly) 500 may also be used to help control the operation of device 1000 and is mounted in compartment 1011 when device 1000 is assembled, as seen in FIG. 3. Assembly 500 preferably includes a transformer that increases the voltage to ion generator 100 in order for it to generate ions.

Figure 8:
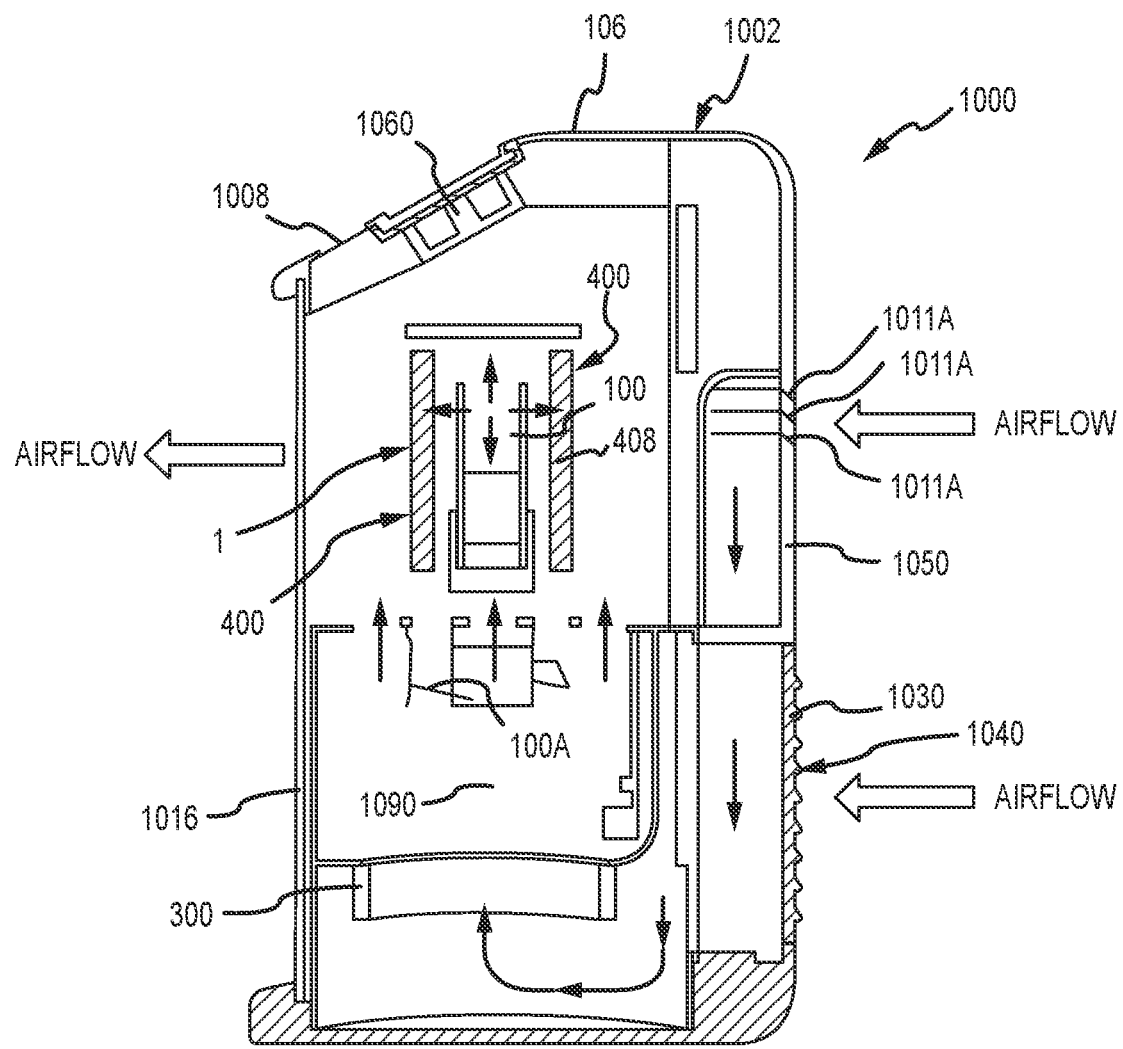
FIG. 8 is a cross-sectional view of the air ionization device of FIG. 1 showing one air path through the device.
Figure 9:
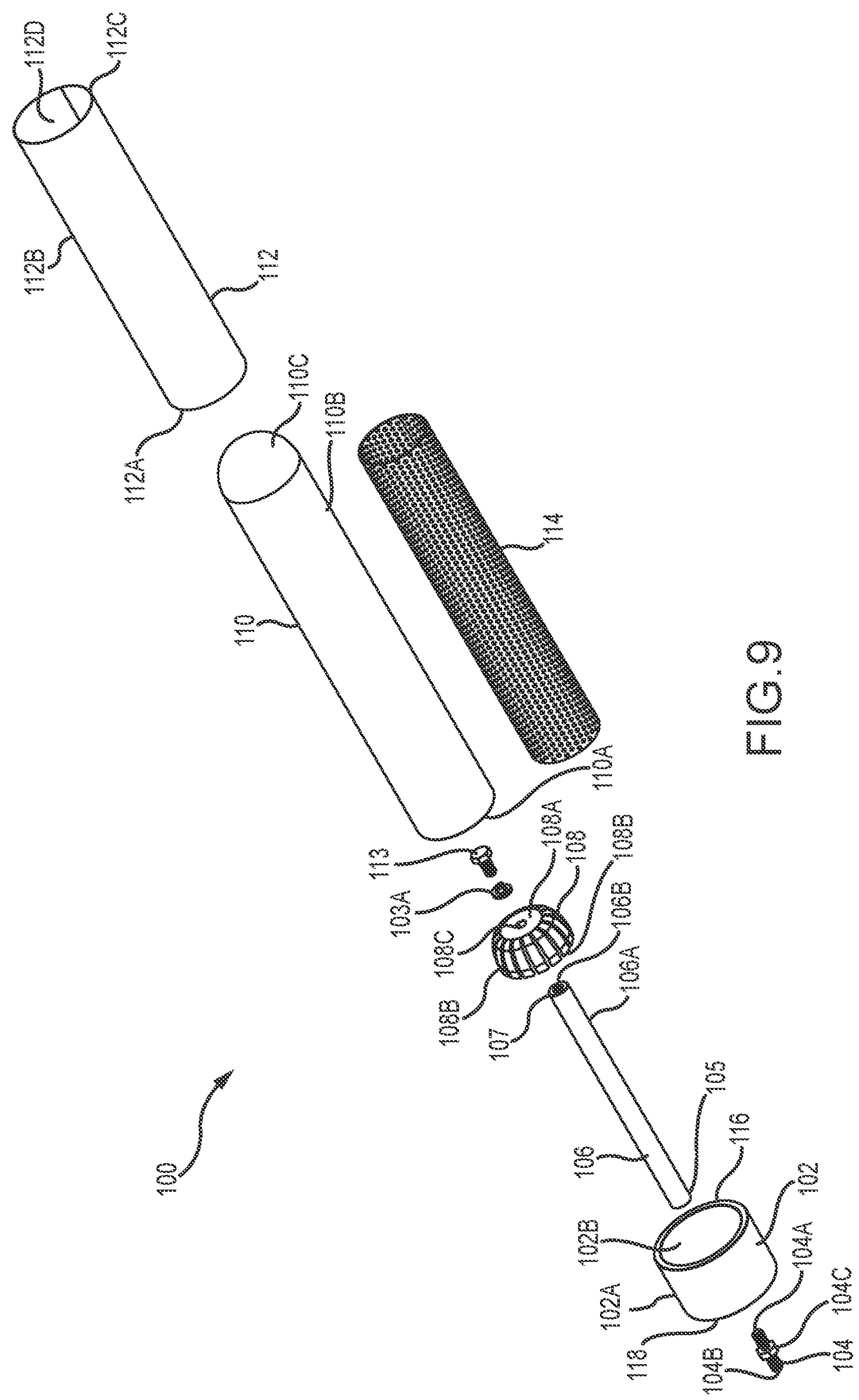
FIG. 9 is an exploded view of an ionization module (or ion generator) according to aspects of the invention.
Figure 10:
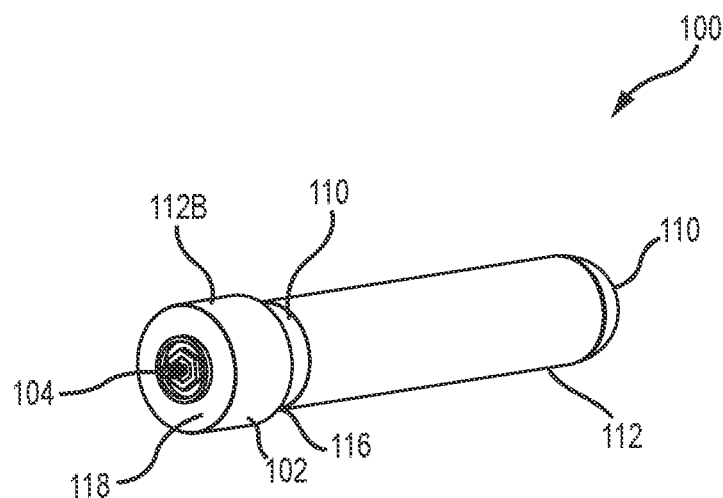
FIG. 10 is an assembled, perspective side view of the ionization module of FIG. 9.
Figure 11:
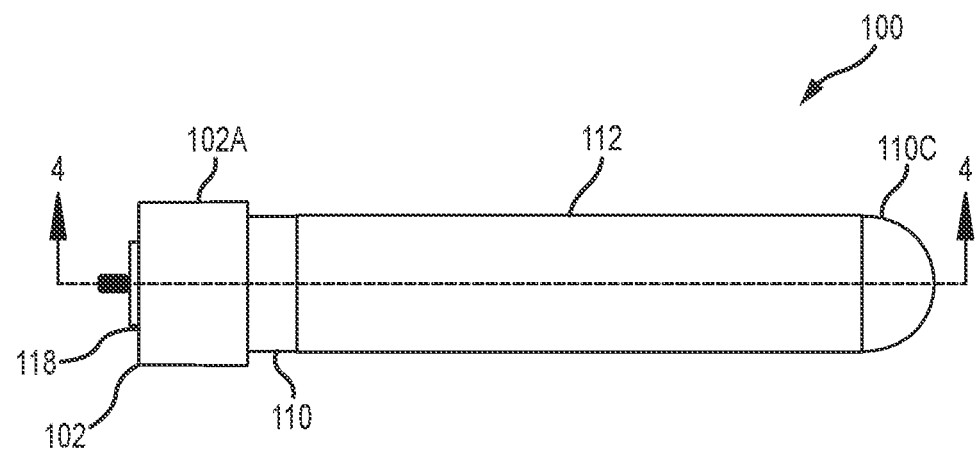
FIG. 11 is an assembled, side view of the ionization module of FIG. 9.
Figure 12:
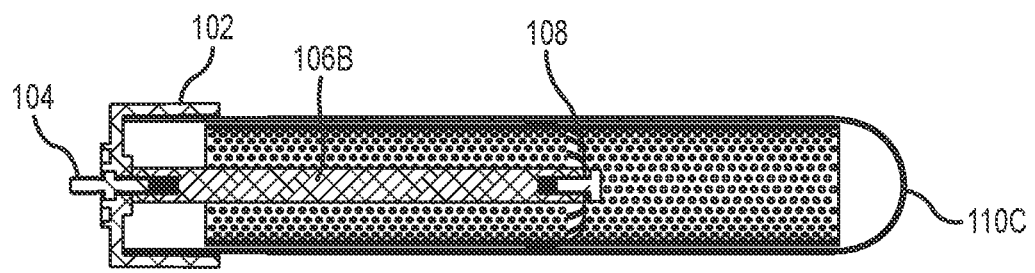
FIG. 12 is a cross-sectional, side view of the ionization module of FIG. 11 taken along lines A-A.
Figure 13:
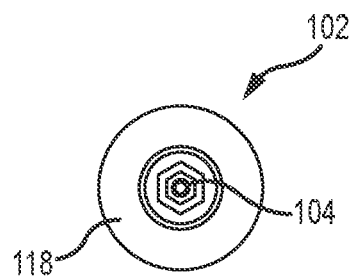
FIG. 13 is an end view of the air ionization module of FIG. 10.
Figure 14:
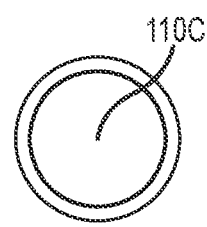
FIG. 14 is the opposite end view of the air ionization module of FIG. 10.

As shown in FIG. 8, air from outside of device 1000 preferably enters through one or more openings 1011A at the back 1010, and also through filter 1040. The air primarily moves through cavity 1002A by the operation of at least one fan 300. Fan 300 moves air upwards towards and around ionization unit 1. Some of the air moved upwards by fan 300 reaches a second (and optional) fan 100A, which moves the air into an air space between ion generator 100 and the ozone catalyst 408, which in this embodiment is included in ozone removal assembly 400. This air is ionized by ion generator (also referred to as an ionization module) 100 and the pressure generated by the fan 100A (and/or fan 300) moves the air through the ozone removal assembly 400, where it contacts the ozone catalyst 408 and has at least some ozone removed.

The air moves out of inner cavity 1002A (primarily due to pressure generated by fan 300) through any suitable opening, such as through openings in the facing 1016. In this embodiment, not all of the air entering cavity 1002A is moved past ion generator 100 and ionized in each pass through device 1000. The amount that is ionized could be any amount from about 5% and about 40%, such as 5%-10%, 5%-15%, 5%-20%, 5%-25%, 5%-30%, 5%-35%, 5%-40%, 10%-20%, 10%-25%, 10%-30%, 10%-35%, 10%-40%, 15%-20%, 15%-25%, 15%-30%, 15%-35%, 15%-40%, 20%-25%, 20%-30%, 20%-35%, or 20%-40%.

Ionization Unit and Ion Generator

Device 1000 preferably includes ionization unit 1 that has an ion generator 100 and ozone removal catalyst 408. Ozone catalyst 408 is preferably contained in an ozone removal assembly 400 that at least partially surrounds the ion generator 100. As previously mentioned, air is moved into a space between the ion generator 100 and the ozone removal assembly 400 in order for ions to be displaced into the air, which helps remove particulates from the air.

In this embodiment, there is a second fan 100A attached to ionization unit 100, wherein second fan 100A also moves air upward and past ion generator 100. One fan, more than two fans, or any suitable method or device, however, may be used to move air past ion generator 100, past ozone catalyst 408, and out of device 1000 and into the space in which device 1000 is positioned.

Turning now to FIG. 8, Ionization unit 1 as shown preferably has an ion generator 100 with an end cap (or "base") 102, an adapter 104, a coupler 106, an ion dispenser 108, a tube 110, an outer electrode 112, and an inner electrode 114. Base 102 is preferably comprised of any suitable plastic, for example injection-molded ABS although any suitable material may be used. The purpose of base 102 is to receive coupler 106, ion dispenser 108, and tube 110.

Coupler 106 has a first end 105, a second end 107, an outer surface 106A, and a passageway 106B extending therethrough. In some embodiments, coupler 106 comprises a hollow aluminum rod. Moreover, coupler 106 may comprise a solid bar with an internal thread on each end. Coupler 106 is configured to conduct electricity.

Adapter 104 as shown is a threaded shaft that bases through an opening (not shown in these Figures) of second end 118 of base 102 and is threadingly received in a passageway 106B at the first end 105 of coupler 106. The opening in second end 118 may also be threaded so as to threadingly receive adapter 104. In the embodiment shown, adapter 104 is a threaded shaft with a first end 104A and a second end 104B. A nut 104C is threadingly received on the threaded shaft, end 105 of coupler 106 is aligned with the opening on the inside of second end 118. First end 104A passes through the opening and is threadingly received in passageway 106B of coupler 106 to retain coupler 106 against second end 118. In some exemplary embodiments, adapter 104 may comprise a solid stainless steel (or other conductive material) adapter with threaded ends and a central integral hex feature to facilitate rotation thereof.

An ion dispenser (also called an "umbrella shaped conductor") 108 is attached to second end 107 of coupler 106. Ion dispenser 108 may be configured with an umbrella-like shape as shown, or be configured in any suitable shape. Ion dispenser 108 operates to dispense electricity into inner electrode 114, and is preferably comprised of stainless steel (for example, stainless steel having a thickness of between about 0.006 inches and about 0.015 inches), has a top 108A for attachment to coupler 106, and has a plurality of downward extending fingers 108B. In this preferred embodiment, ion dispenser 108 is attached to coupler 106 by aligning an opening in top 108A with passageway 106B at end 107 of coupler 106. Then fastener 113, which as shown is a bolt, is passed through opening 108C and threaded into passageway 106B. A lock washer 113A may be positioned between top 108A and the head of fastener 113.

Inner electrode 114 typically comprises a rolled perforated aluminum sheet, but may comprise any suitable material or combination of materials configured to act as a first electrode for purposes of ionization.

Outer electrode 112 typically comprises a tubular stainless steel wire mesh, for example a 0.008 in diameter Type 316 stainless steel wire mesh configured with a 20×20 per square inch grid. However, outer electrode 112 may comprise any suitable material or combination of materials configured to act as a second electrode for purposes of ionization.

A tube 110 is preferably glass (for example, comprised of borosilicate) and retains coupler 106 and ion dispenser 108. Tube 110 is also operative to insulate inner electrode 114 from outer electrode 112 and thus permit the development of a voltage potential therebetween in order to facilitate ionization. Tube 110 has a first, open end 110A, an outer surface 110B, and a second end 110C. Preferably, after cap 102, coupler 106, and ion dispenser 108 are assembled, inner electrode 114 is placed within tube 110, the first end 110A of tube 110 is positioned over ion dispenser 108 and coupler 106, and is received in cap 102 in a snug to slightly loose fit. Outer electrode 112, which has a first end 112A, an outer surface 112B, a second end 112C, and an inner passage 112D, is positioned over tube 110. In the preferred embodiment shown, outer electrode 112 does not cover second end 110C of tube 110 or extend to cap 102.

A tube used with this disclosure preferably has one open end 110A and one closed end 110C, as shown. A tube could, however, have two open ends and be supported at each end, and even possibly supported at one or more positions along its length by non-conductive insulators. Generally speaking, for tubes of the same diameter, the longer the tube the greater the ionization because of the greater surface area. Thus, the tube length may be selected to achieve a particular amount of ionization.

In this embodiment, when ion generator 100 is assembled, coupler 106 and ion dispenser 108 are positioned approximately 50-60% inside the length of tube 110. In this manner, electrical current is delivered to approximately the center of inner electrode 114. The tube lengths (100) may be varied to control amount of ionization that occurs.

Ozone Removal Catalyst and Ozone Removal Assembly

Figure 15:
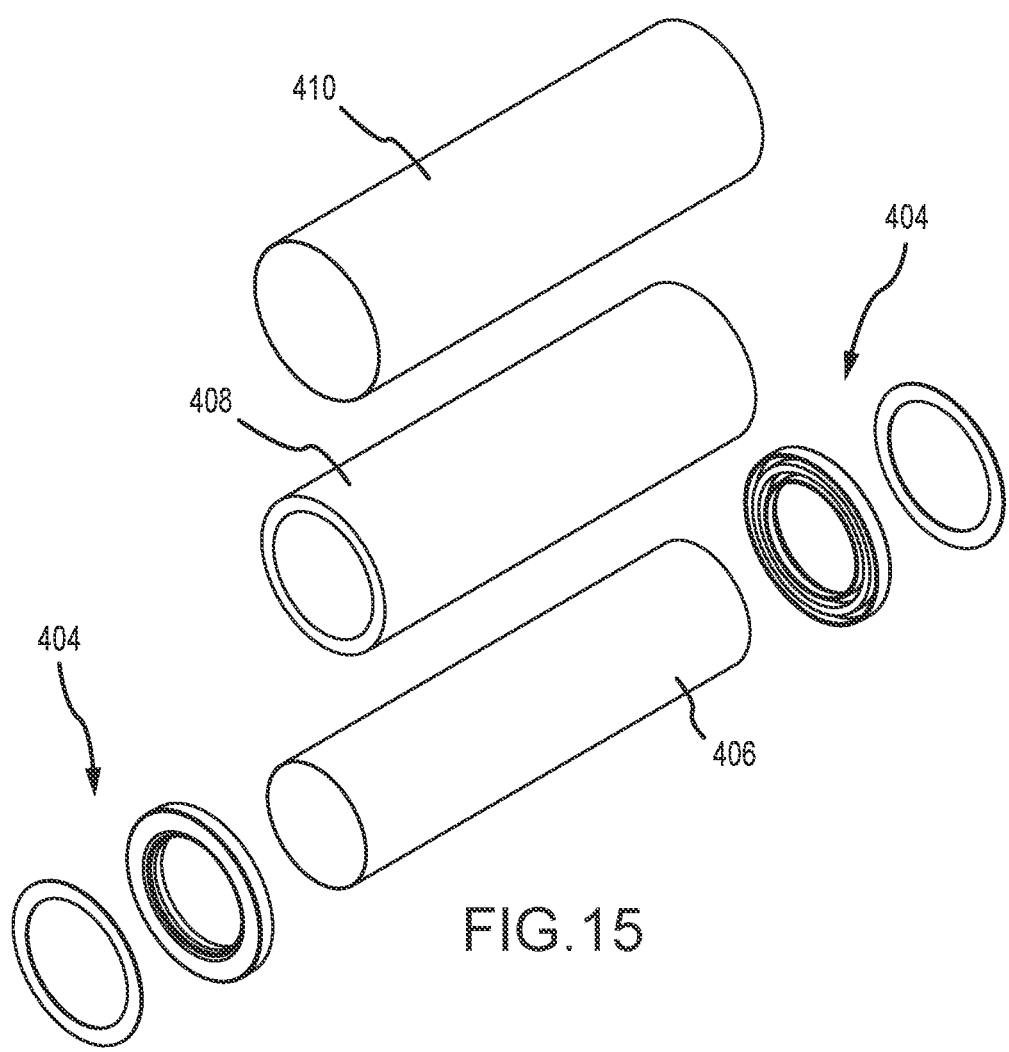
FIG. 15 is an exploded view of an ozone removal assembly according to aspects of the invention.
Figure 16:
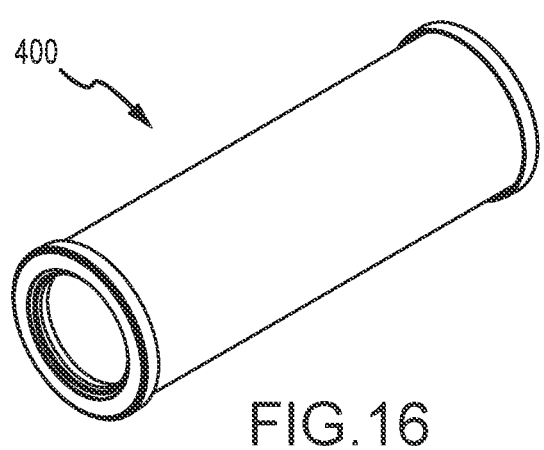
FIG. 16 is a perspective, side view of the assembled ozone removal assembly of FIG. 15.
Figure 17:
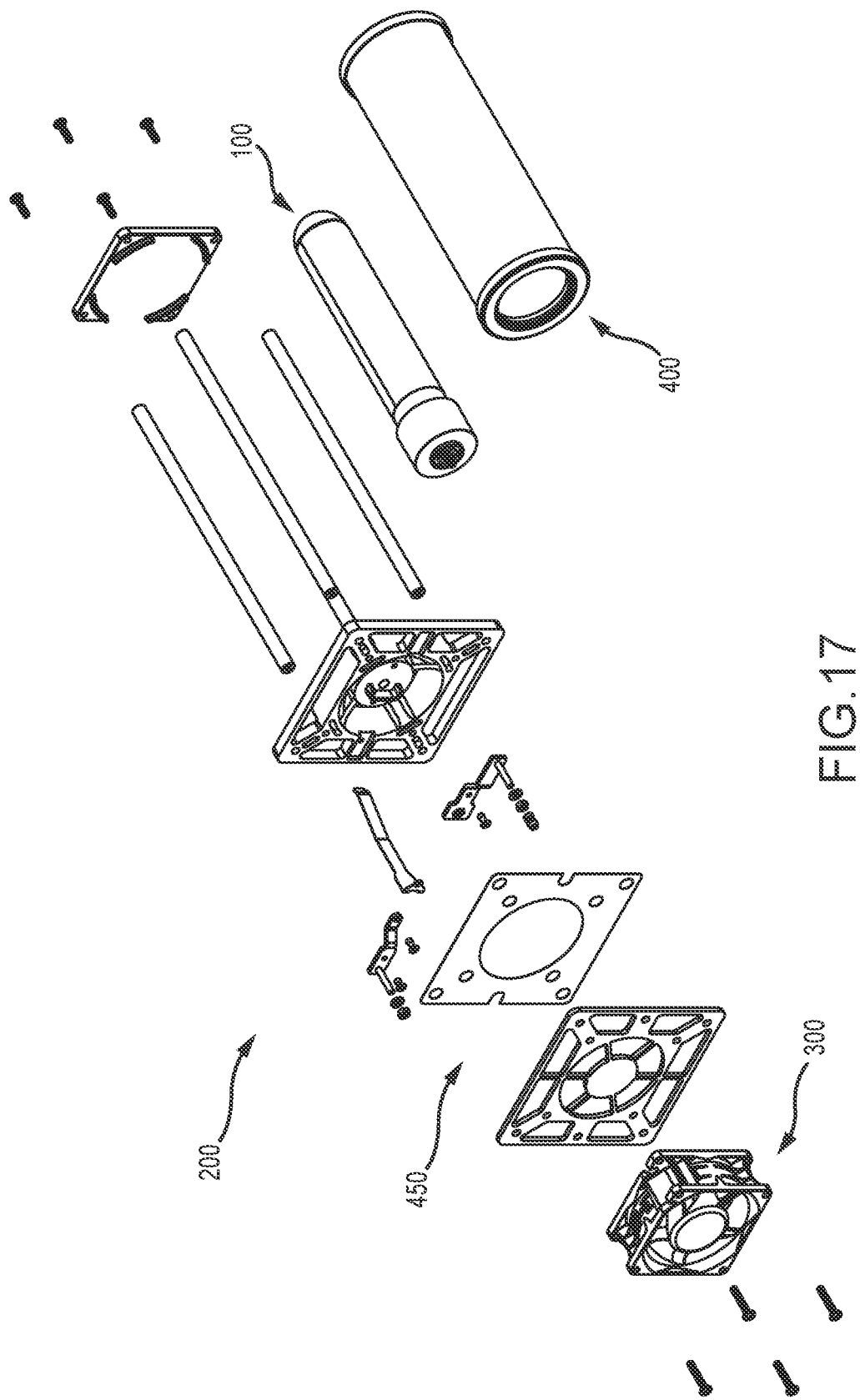
FIG. 17 is an exploded view of an air ionization unit according to aspects of the invention.
Figure 18:
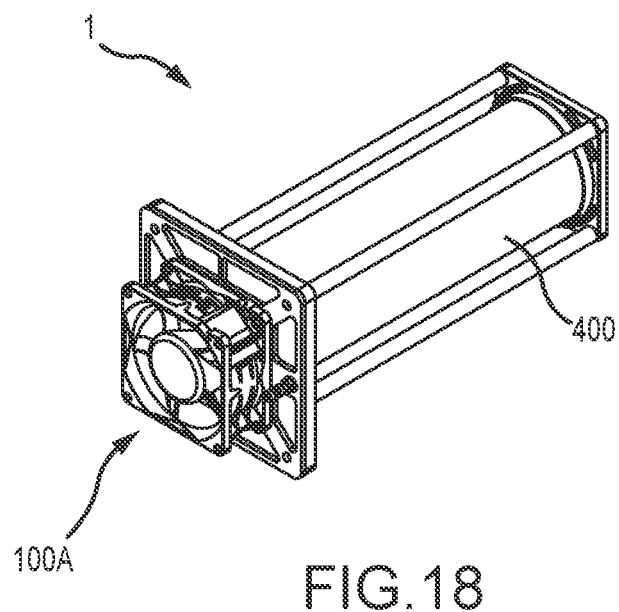
FIG. 18 is an assembled, perspective side view of the air ionization unit of FIG. 17.
Figure 19:
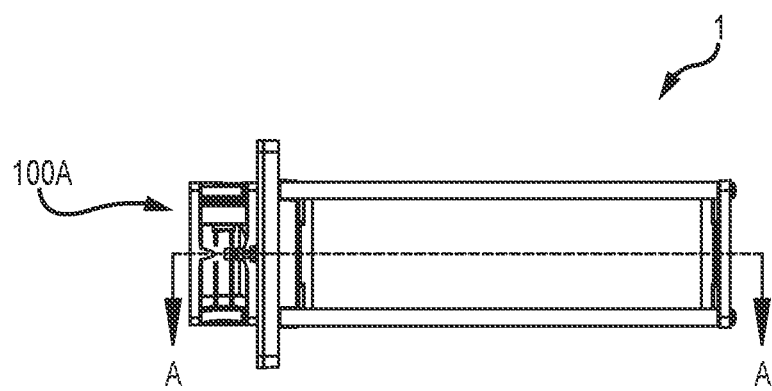
FIG. 19 is an assembled, side view of the ionization unit of FIG. 17.
Figure 20:
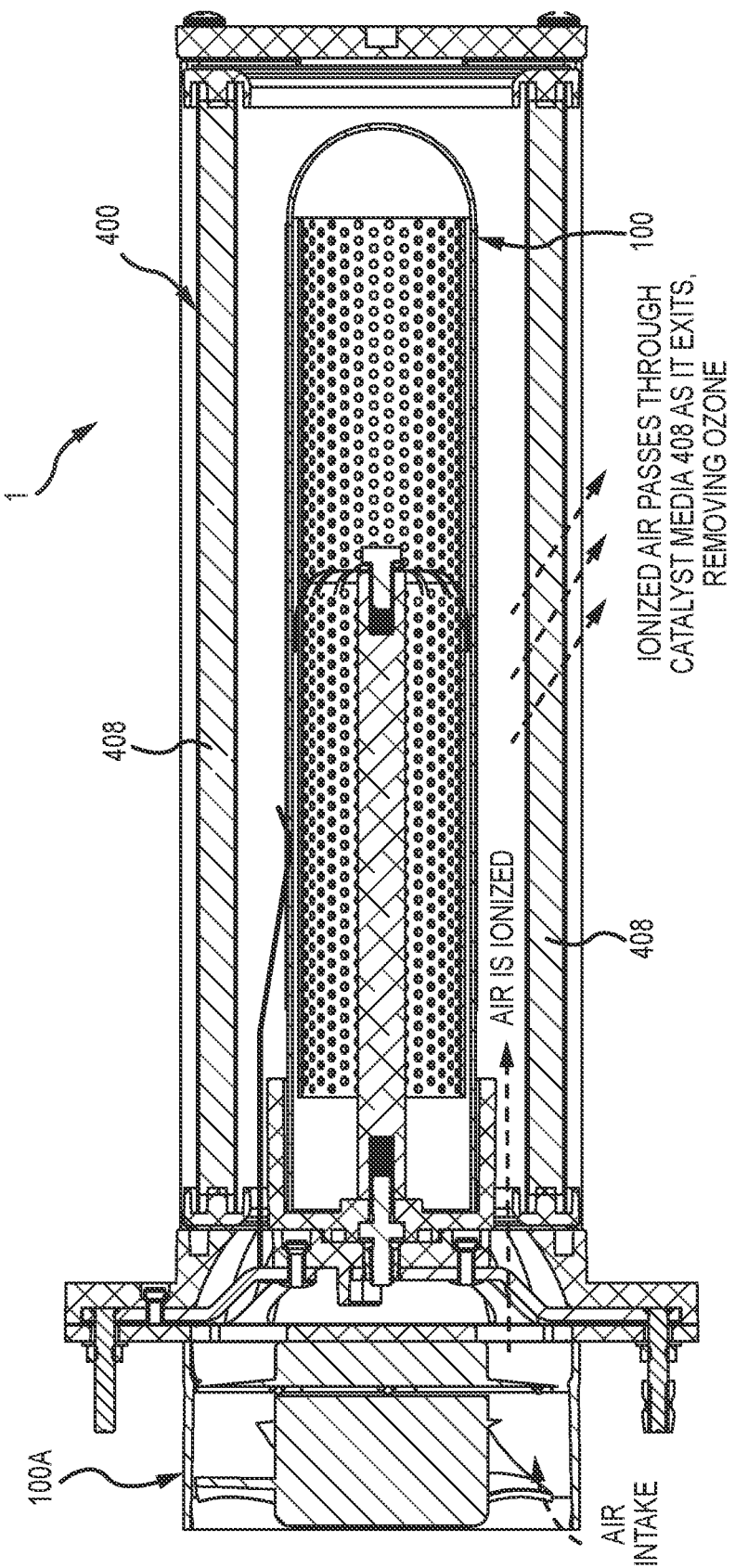
FIG. 20 is a cross-sectional, side view of the ionization module of FIG. 19 taken along lines A-A.
Figure 21:
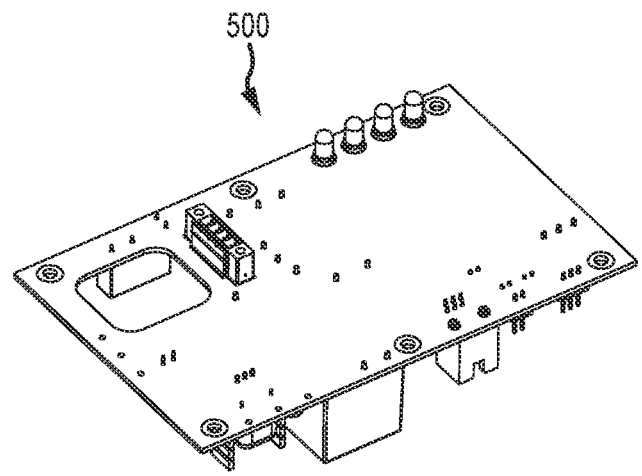
FIG. 21 is a rear, perspective view of a control unit according to aspects of the invention.

With reference now to FIGS. 15 and 16, an exemplary ozone removal assembly 400 comprises a tubular inner wall 406, a tubular outer wall 410, and a pair of ends 404. Inner wall 406, outer wall 410, and ends 404 may be coupled together to form a container for ozone removal (or "ozone catalyst") catalyst 408. Inner wall 406 and outer wall 410 are coupled to a first end 404 (for example, via RTV silicone). First end 404 is disposed on a surface, and the space between inner wall 406 and outer wall 410 is filled with ozone catalyst 408. Second end 404 is then coupled to inner wall 406 and outer wall 410, securing ozone catalyst 408 in the resulting assembly. Inner wall 406 and outer wall 410 are configured to be at least partially permeable to air. For example, inner wall 406 and outer wall 410 may comprise rolled stainless steel mesh screen or the like.

Ozone catalyst 408 is configured to convert, neutralize, and/or otherwise remove and/or reduce ozone. Ozone catalyst 408 may also be referred to as a "catalyst bed", "reaction bed", or "ozone destruction catalyst." Ozone catalyst 408 may be granulated or otherwise shaped or formed. Ozone catalyst 408 typically comprises manganese dioxide, copper oxide, and/or the like, or combinations thereof. Ozone catalyst 408 may comprise Carulite 200 provided by Cams Corporation (Peru, Ill.). However, any suitable catalyst configured to neutralize and/or remove ozone from an airstream may be utilized.

Ionization Unit Cartridge

FIGS. 17-20 show an ionization and filter cartridge 200 according to a preferred embodiment of the invention. Cartridge 200 includes previously described module 100. It also generally includes a housing and support structure, a fan assembly (or fan) 100A, an ozone removal assembly 400, and an air filter 450. Air filter 450 may comprise polypropylene, natural fibers, and/or any suitable material. Air filter 450 is operative to reduce the amount of dust and other airborne particulates entering ozone removal assembly 400.

The support structure of cartridge 200 includes a section for supporting module 100 and ozone removal assembly 400, and a section for supporting fan assembly 100A, wherein, in the preferred embodiment, when cartridge 200 is fully assembled, it is a single unit that may be removed and replaced from device 1000 when desired.

Electronic Controls

FIGS. 20-24 show electronic controls 500, which are preferably configured to control ion generator 100 to generate more negative ions than positive ions, at least 60% negative ions, or in excess of 66% negative ions, or at least 70% negative ions, or at least 80% negative ions, or at least 90% negative ions. In this manner, ion generator 100 generates a net excess of negative ions, and thus improved air filtration and clearing is achieved. Alternatively, controls 500 and device 1000 with ion generator 100 can generate an equal number of positive and negative ions, or more positive ions than negative ions, such as at least 60% positive ions, at least 10% positive ions, at least 70% positive ions, or at least 90% positive ions.

Electronic controls 500 preferably pulse power convertors 520 in a manner suitable to positively bias power convertors 520 with respect to circuit ground; this results in generation of excess negative ions in module 100.

Additionally, electronic controls 500 may further comprise and/or communicate with various inputs (e.g., sensors) which monitor ionization levels, the density of particulates in the air, the ambient humidity, temperature, and/or other parameters. Based at least in part on the sensor inputs, electronic controls 500 adjust the operation of device 1000 to achieve a desired level of filtration and/or ionization level.

All of the electronics used to control ion generator 100 and other aspects of operation of device 1000 are referred to as the control system.

With reference to FIGS. 20-24, electronic controls 500 typically comprise various electronic components, for example: a printed circuit board; RF module 510 for wireless communication via a suitable wireless protocol or protocols (for example, IEEE 802.11 ("WiFi"), IEEE 802.15.4 ("ZigBee"), Bluetooth, GSM, and/or any suitable protocol); power convertor(s) 520 for creating, modulating, transforming, and/or converting AC and/or DC current, for example for use in operating module 100 to produce ions; wired communication and/or input programming port(s) 530; together with various resistors, capacitors, inductors, transistors, diodes, light-emitting diodes, switches, traces, jumpers, fuses, amplifiers, antennas, and so forth as are known in the art. Electronic controls 500 may further comprise a microprocessor and/or microcontroller (for example, an 8-bit or 16-bit microcontroller, such as the PIC16F1503T-I/SL microcontroller offered by MicroChip Corporation of Chandler, Ariz.). The microcontroller is operative for algorithmic (i.e., pre-programmed) operation, as well as responsive (i.e., pursuant to sensor inputs, communications, etc.) operation of system 600.

In one operating mode, electronic controls 500 are configured to operate module 100 at an 80% duty cycle (for example, 4 minutes in an ion generation mode, followed by one minute powered down, followed by 4 minutes in an ion generation mode, and so forth). In another operating mode, electronic controls 500 are configured to operate module 100 at a 100% duty cycle (always on). However, any suitable duty cycle may be utilized.

In various exemplary embodiments, electronic controls 500 are configured to generate up to 6000 volts at frequencies between 1 kHz and 2 kHz for use in ionization. Electronic controls 500 typically draw between about 700 milliamps and about 900 milliamps. Power supplied to module 100 via electronic controls 500 may be digitally managed, for example via a pulse width modulation (PWM) technique utilizing a fixed voltage and variable duty cycle. Moreover, operating parameters for electronic controls 500 may be remotely managed.

Electronic controls 500 may employ a "white noise" mode wherein power convertors 520 are turned on and/or off via randomized timing to change frequency so as to eliminate or partially eliminate vibration and resonating. The amount of time varies randomly by using a pseudo-random number generator which outputs a new number after each pulse. In one embodiment, the number ranges from 0 to 500. This is added to a constant of 500, which sets the time, in microseconds, from start of pulse to start of next pulse. In this manner, transformer "whine" or "power line hum" may be reduced and/or eliminated, making the resulting system quieter and/or more suitable for indoor use.

Hi-voltage Pulsing Algorithm: One high-voltage pulse consists of turning on a voltage source to the primary side of the fly-back transformer for a set amount of time, then turning it off quickly. The next pulse occurs between 500 uS and 1000 uS later.

In another operating mode, electronic controls 500 may be configured to operate system 600 in an "ozone depletion mode" whereby module 100 is powered down and does not create ionization, but air is still passed through ozone catalyst 408, for example responsive to operation of fan assembly 100 (and/or as a result of ambient airstream movement, for example in an HVAC duct). In this manner, device 1000 is operative to remove ozone from the ambient air.

Electronic controls 500 preferably monitor the performance of module 100 and/or ozone removal assembly 400, and may signal when a component of device 1000 needs replacing (for example, due to deterioration of ionization components in module 100, due to dust accumulation on ozone catalyst 408 in module 400, and/or the like).

For example, electronic controls 500 may monitor fan 100A speed and current draw, as well as module 100 voltage and current draw. Device 1000 may be shut down and/or restarted if an anomaly is detected. Additionally, electronic controls 500 may monitor status and error conditions, turn an ozone depletion mode on or off, monitor temperature limits for operation, and/or adjust a duty cycle associated with operation of module 100.

Figure 22:
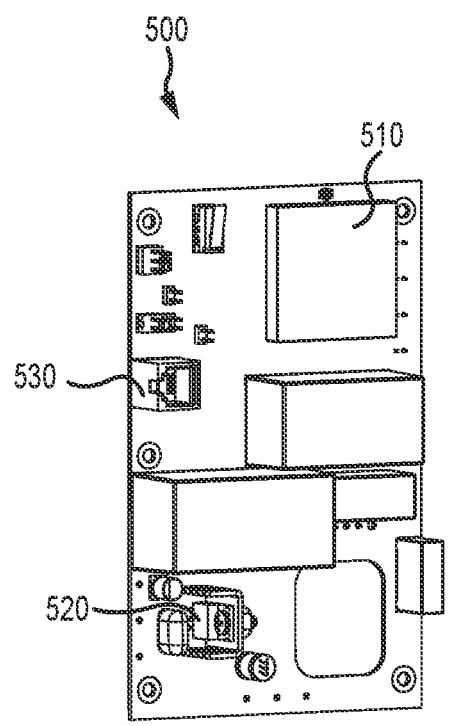
FIG. 22 is a front, perspective view of the control unit of FIG. 21.

In some embodiments, with reference to FIG. 22, system 1000 may further comprise a control panel 1060. Control panel 1060 comprises a display and various inputs, and/or buttons. Control panel 1060 is in wired and/or wireless communication with control electronics 500. Via control panel 1060, a user may view statistics regarding operation of device 1000, give commands to device 1000, view error messages or other system 600 communications.

Figure 25:
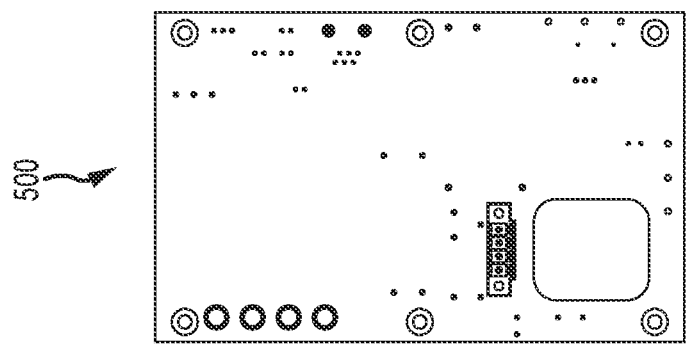
FIG. 25 is a rear view of the control unit of FIG. 21.
Figure 24:
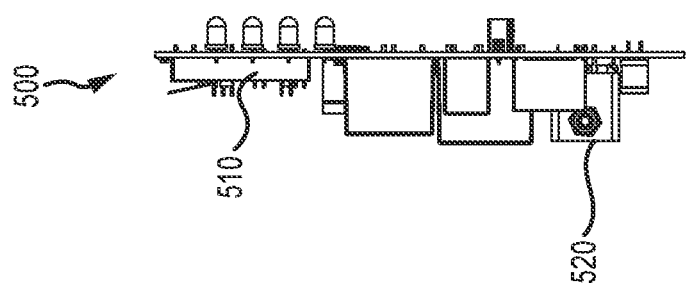
FIG. 24 is a side view of the control unit of FIG. 21.
Figure 23:
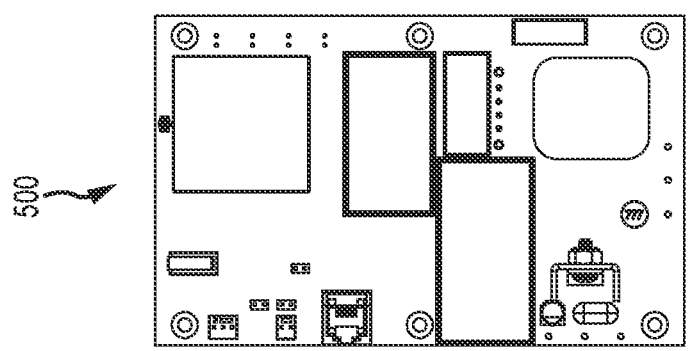
FIG. 23 is a front view of the control unit of FIG. 21.
Figure 26:
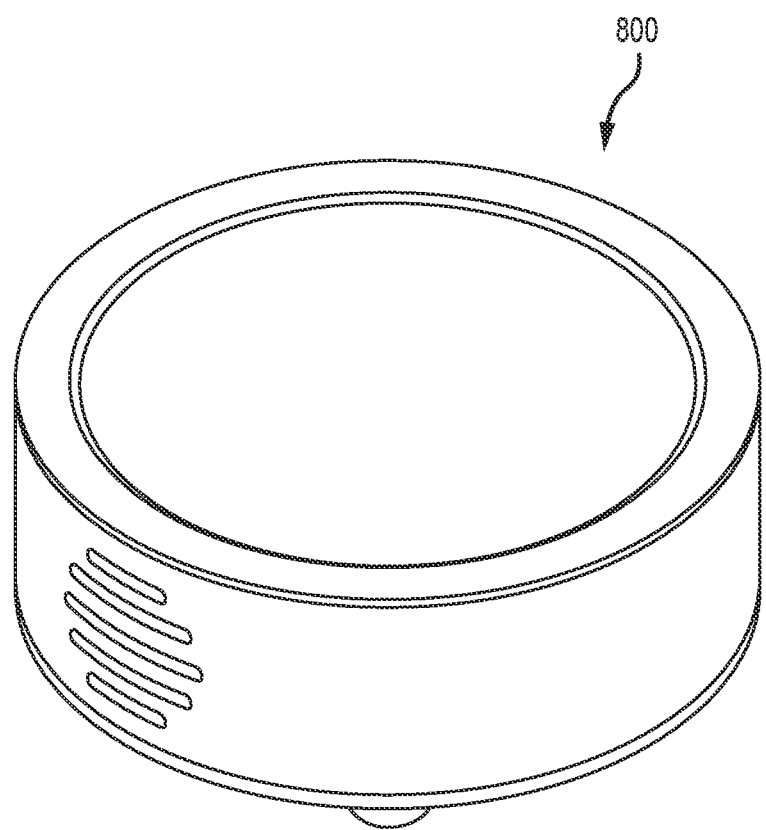
FIG. 26 is a front, perspective view of a remote sensor that may be used with disclosed embodiments.

Device 1000 may further comprise one or more remote sensors 800, which is shown in FIGS. 25-26. Remote sensor 800 would be in wired and/or wireless communication with control electronics 500. Remote sensor 800 could comprise various sensors, for example a temperature sensor, particulate sensor, ozone sensor, carbon monoxide sensor, and/or humidity sensor. Responsive to information received from remote sensor 800, control electronics 500 may modify operation of device 1000, for example: (1) turning module 100 on or off, (2) turning fan 100A or fan 300 on or off, (3) operate device 1000 in an ozone depletion mode when ambient ozone is detected above a target threshold until the ambient ozone level is below a target threshold, (4) increase the duty cycle of module 100 in order to generate increased ionization and thus increase the rate of particulate removal when remote sensor 800 reports that particulates are above a target threshold.

One or more remote sensors 800 may be battery powered, or may be configured to be plugged into a power outlet.

Some non-limiting examples of this disclosure follow:

Example 1

An air ionization device, comprising:
(a) a portable housing including an air-intake port through which air can pass, an air discharge through which air can pass, and an inner cavity;
(b) an ion generator in the inner cavity; and
(c) an ozone removal catalyst at least partially surrounding the ion generator, the ozone removal catalyst being configured to remove at least some ozone from the air, wherein the ozone removal catalyst at least partially surrounds the ion generator.

Example 2

The air ionization device of example 1, wherein the ion generator is configured to generate more negative ions than positive ions.

Example 3

The air ionization device of example 1 or 2, wherein the ion generator is configured to generate at least 60% negative ions.

Example 4

The air ionization device of any of examples 1-3, wherein the ozone removal catalyst is part of an ozone removal assembly that at least partially surrounds the ion generator.

Example 5

The air ionization device of any of examples 1-4 that further includes a first fan in the inner cavity.

Example 6

The air ionization device of example 5, wherein the first fan is beneath the ion generator and is configured to blow air towards the ion generator.

Example 7

The air ionization device of any of examples 1-6, wherein the portable housing has a back surface and the air-intake port is at the back surface.

Example 8

The air ionization device of any of examples 1-7, wherein the portable housing has a base, a top, and one or more side walls connecting the base to the top.

Example 9

The air ionization device of any of examples 1-8 that further comprises an annular facing.

Example 10

The air ionization device of any of examples 1-9 that further comprises an air filter at one or more of: the air-intake port, the air discharge, and between a fan and the ion generator.

Example 11

The air ionization device of any of examples 1-9 that further includes an air filter at the air-intake port.

Example 12

The air ionization device of any of examples 1-11 that further comprises a control system that measures an ion count in the air and powers the ion generator based at least in part on the measured ion count in the air.

Example 13

The air ionization device of example 12, wherein the control system also measures at least one of an ozone level, an air temperature, a particulate level, a carbon monoxide level, and a humidity.

Example 14

The air ionization device of any of examples 12-13, wherein the ion generator comprises an ion dispenser configured to receive electrical current responsive to the operation of the control system.

Example 15

The air ionization device of any of examples 1-14, wherein the ion generator further comprises an inner electrode electrically coupled to the ion dispenser, the inner electrode comprising a perforated aluminum sheet.

Example 16

The air ionization device of example 15, wherein the ion generator further comprises:
(a) a glass tube disposed at least partially around the inner electrode; and
(b) an outer electrode disposed at least partially around the glass tube, the outer electrode comprising a tubular stainless steel mesh screen.

Example 17

The air ionization device of any of examples 1-16, wherein the ozone removal assembly comprises:

(a) an inner stainless steel mesh screen forming a first tube;
(b) an outer stainless steel mesh screen forming a second tube; and
(c) an ozone catalyst disposed between the first tube and the second tube.

Example 18

The air ionization device of example 17, wherein the ozone removal assembly further comprises a pair of end caps coupling the first tube and the second tube.

Example 19

The air ionization device of any of examples 1-18, wherein the ion generator is tubular, the ozone removal assembly is tubular, and the ion generator is disposed within the ozone removal assembly, and there is an airspace separating the ion generator from the ozone removal assembly.

Example 20

The air ionization device of example 19, wherein the airspace is cylindrical.

Example 21

The air ionization device of example 19 that further comprises a second fan configured to move air into the airspace between the ion generator and the ozone removal assembly, wherein the second fan is between the first fan and the ion generator.

Example 22

The air ionization device of example 21, wherein responsive to operation of the second fan, air enters the airspace and exits the air ionization system by passing through the ozone catalyst.

Example 23

The air ionization device of any of examples 12-14 that further comprises a sensor in communication with the control system, wherein the sensor measures at least one of an ozone level, an air temperature, a particulate level, a carbon monoxide level, and a humidity.

Example 24

The air ionization device of example 23, wherein the sensor communicates the measurements to the control system.

Example 25

The air ionization device of example 21 or 22 that further comprises an air filter disposed between the second fan and the airspace.

Example 26

The air ionization device of any of examples 10, 11, or 25, wherein the air filter comprises at least one of polypropylene or cotton.

Example 27

The air ionization device of any of examples 1-26, wherein the ion generator and ozone removal assembly are part of a modular unit that may be removed from the air ionization device and replaced.

Example 28

The air ionization device of example 27, wherein the modular unit also includes the second fan.

Example 29

The air ionization device of example 28, wherein the modular unit also includes a filter positioned between the second fan and the ion generator.

Example 30

The air ionization device of any of examples 1-29 that weighs from 12 lbs. to 22 lbs.

Example 31

A method of cleaning air using a portable air ionization device, the method comprising:
(a) placing the air ionization device into a space that includes air;
(b) activating the air ionization device;
(c) moving air from the space through an input port of the air ionization device, into an inner cavity of the air ionization device, and into contact with an air ionization generator that ionizes the air;
(d) moving the ionized air into contact with an ozone-removal catalyst after the air has been ionized; and
(e) moving the air through a discharge and back into the space.

Example 32

The method of example 31, wherein a fan is operated when the air ionization device is turned on.

Example 33

The method of example 32, wherein the operation of the fan moves the air.

Example 34

The method of any of examples 31-33, wherein the air is moved upwards in the inner cavity and into contact with the air ionization generator.

Example 35

The method of any of examples 31-34, wherein at least some of the air is moved outward after it is ionized.

Example 36

The method of any of examples 31-35, wherein the air is filtered inside of the inner cavity before it is ionized.

Example 37

The method of any of examples 31-36, wherein the air is filtered before entering the inner cavity.

Example 38

The air ionization device of example 13, wherein the control system powers the ion generator based on one or more of the measured ozone level, air temperature, particulate level, carbon monoxide level, and humidity.

Example 39

The air ionization device of any of examples 1 or 4-30, wherein the ion generator is configured to generate an equal number of positive and negative ions.

Example 40

The air ionization device of any of examples 1 or 4-30, wherein the ion generator is configured to generate more positive ions than negative ions.

Example 41

The air ionization device of any of examples 1-30 or 38-40 that further includes an air sensor inside of the portable housing.

Example 42

The air ionization device of any of examples 1-30 or 38-41 that further includes an air sensor remote to the portable housing.

Example 43

The air ionization device of any of examples 1-30 or 38-42 that further includes at least one opening through which air can enter the inner cavity in addition to the air-intake port.

Example 44

The air ionization device of example 43, wherein the at least one opening is above an air sensor positioned in the inner cavity, and the air sensor is configured such that air entering the at least one opening contacts the air sensor.

Example 45

The air ionization device of example 44, wherein the air sensor is above the air-intake.

Example 46

The air ionization device of any of examples 1-30 or 38-45 that further includes electric controls that turn one or more power converters off and on using random timing.

Example 47

The air ionization device of example 46, wherein the random timing is created using a pseudo-random number generator.

Example 48

The air ionization device of example 46 or example 47, wherein a high voltage pulse occurs between 400 uS and 1000 uS after a prior high voltage pulse.

In the foregoing specification, the invention has been described with reference to various embodiments. However, one of ordinary skill in the art appreciates that various modifications and changes can be made without departing from the scope of the present invention as set forth in the claims below. Accordingly, the specification is to be regarded in an illustrative rather than a restrictive sense, and all such modifications are intended to be included within the scope of the present invention. Likewise, benefits, other advantages, and solutions to problems have been described above but are not critical, required, or essential to any of the claims.

What is claimed is:

1. An air ionization device, comprising:
   (a) a housing including an air-intake port through which air can pass, an air discharge through which air can pass, and an inner cavity;
   (b) an ion generator in the inner cavity; and
   (c) an ozone removal catalyst in the inner cavity between the ion generator and the air discharge, the ozone removal catalyst being configured for removing at least some ozone from the air, wherein the ozone removal catalyst is part of an ozone removal assembly that at least partially surrounds the ion generator and comprises (a) an inner stainless steel mesh screen forming a first tube, (b) an outer stainless steel mesh screen forming a second tube; and (c) an ozone catalyst disposed between the first tube and the second tube.

2. The air ionization device of claim 1, wherein the ion generator is configured to generate more negative ions than positive ions.

3. The air ionization device of claim 1, wherein the ion generator is configured to generate at least 60% negative ions.

4. The air ionization device of claim 1 that further comprises a first fan in the inner cavity.

5. The air ionization device of claim 1 that further comprises one annular facing through which air can pass.

6. The air ionization device of claim 1 that further comprises an air filter at the air-intake port.

7. The air ionization device of claim 1 that further comprises a control system that measures an ion count in the air and powers the ion generator based at least in part on the measured ion count in the air.

8. The air ionization device of claim 7, wherein the control system also measures at least one of an ozone level, an air temperature, a particulate level, a carbon monoxide level, and a humidity.

9. The air ionization device of claim 7, wherein the ion generator comprises an ion dispenser configured to receive electrical current responsive to operation of the control system.

10. The air ionization device of claim 7 that further comprises a sensor in communication with the control system, wherein the sensor measures at least one of an ozone level, an air temperature, a particulate level, a carbon monoxide level, and a humidity, and wherein the sensor communicates the measurements to the control system.

11. The air ionization system of claim 10, wherein the sensor is inside the portable housing.

12. The air ionization system of claim 11, wherein the sensor communicates wirelessly with the control system.

13. The air ionization device of claim 1, wherein the ozone removal assembly further comprises a pair of end caps coupling the first tube and the second tube.

14. The air ionization device of claim 1, wherein the ion generator is tubular, the ozone removal assembly is tubular, and the ion generator is disposed at least partially within the ozone removal assembly, and there is an airspace separating the ion generator from the ozone removal assembly.

15. The air ionization device of claim 1 that further includes a first fan configured to move air towards the ion generator.

16. The air ionization device of claim 15 that further comprises a second fan that is configured to move air into the airspace between the ion generator and the ozone removal assembly.

17. The air ionization device of claim 16, wherein the second fan is further configured to move the air through the ozone removal catalyst.

18. The air ionization device of claim 17, wherein the sensor is remote to the portable housing.

19. The air ionization device of claim 16, further comprising an air filter disposed between the second fan and the airspace.

20. The air ionization device of claim 1, wherein the ion generator and ozone removal assembly form a modular unit that may be removed from the inner cavity and replaced.

21. The air ionization device of claim 1 that weighs from 10 lbs. to 22 lbs.

22. The air ionization device of claim 1, wherein the ion generator comprises: (i) an inner electrode electrically coupled to the ion dispenser; and (ii) separated from the inner electrode.

23. The air ionization device of claim 1 that at least partially surrounds the ion generator.

* * * * *